(12) United States Patent
Komiya et al.

(10) Patent No.: US 8,366,834 B2
(45) Date of Patent: Feb. 5, 2013

(54) ENDOSCOPE CLEANING/DISINFECTING APPARATUS

(75) Inventors: Takaaki Komiya, Hachioji (JP); Hideto Onishi, Hachioji (JP); Naoya Taya, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/186,805

(22) Filed: Jul. 20, 2011

(65) Prior Publication Data

US 2012/0125385 A1 May 24, 2012

(30) Foreign Application Priority Data

Nov. 24, 2010 (JP) ................................ 2010-261091

(51) Int. Cl.
*B08B 3/00* (2006.01)
(52) U.S. Cl. ...................................... 134/56 R; 134/94.1
(58) Field of Classification Search .................. None
See application file for complete search history.

(56) References Cited

U.S. PATENT DOCUMENTS

| 6,068,815 A | 5/2000 | Oberleitner et al. | |
| 6,379,632 B1* | 4/2002 | Kinoshita et al. | ............ 422/300 |
| 6,656,438 B1* | 12/2003 | Kinoshita et al. | ............ 422/292 |
| 7,758,704 B2* | 7/2010 | Hasegawa et al. | ........... 134/56 R |
| 2008/0115814 A1* | 5/2008 | Hasegawa et al. | ........... 134/56 R |

FOREIGN PATENT DOCUMENTS

| EP | 0 882 457 A2 | 12/1998 |
| EP | 1 121 942 A2 | 8/2001 |
| JP | 2004-121832 | 4/2004 |
| WO | WO 96/00092 A1 | 1/1996 |
| WO | WO 2007/018742 A2 | 2/2007 |

OTHER PUBLICATIONS

Extended European Search Report dated Feb. 14, 2012 issued in counterpart European Patent Application No. 11005991.2.

* cited by examiner

*Primary Examiner* — Michael Barr
*Assistant Examiner* — Jason Ko
(74) *Attorney, Agent, or Firm* — Scully, Scott, Murphy & Presser, P.C.

(57) ABSTRACT

An endoscope cleaning/disinfecting apparatus according to the present invention includes a chemical bottle, an insertion portion, a chemical receiving portion, a blade portion, a first limit switch and a second limit switch. When the chemical bottle is moved to a first position, the first limit switch changes from off to on to detect the first position, when the chemical bottle is inserted to a second position at which an inner face of the chemical receiving portion and a spout portion are aligned to each other, the second limit switch changes from off to on to detect the second position, and when the chemical bottle is inserted to a third position at which a stopper portion is opened, the first limit switch is released by a stepped portion from pressing by the chemical bottle, and thereby changes from on to off to detect the third position.

5 Claims, 7 Drawing Sheets

ENDOSCOPE CLEANING/DISINFECTING APPARATUS

CROSS REFERENCE TO RELATED APPLICATION

This application claims benefit of Japanese Application No. 2010-261091 filed in Japan on Nov. 24, 2010, the contents of which are incorporated by this reference.

BACKGROUND OF THE INVENTION

1. Field of the Invention

The present invention relates to an endoscope cleaning/disinfecting apparatus including a chemical bottle and an insertion portion into which the chemical bottle is inserted.

2. Description of the Related Art

When a chemical bottle is inserted at an angle into an insertion portion of an endoscope cleaning/disinfecting apparatus to set the chemical bottle in the endoscope cleaning/disinfecting apparatus, a stopper portion provided at a top face of a chemical storage portion of the chemical bottle is opened by being broken by a blade portion located at the back of the insertion portion, and as a result, a chemical in the chemical bottle is poured by its own weight into a chemical tank in the endoscope cleaning/disinfecting apparatus via a duct line. The chemical bottle contains, for example, a concentrated solution of a disinfectant used for disinfecting an endoscope or a buffer solution for a disinfectant.

For the chemical bottle setting, Japanese Patent Application Laid-Open Publication No. 2004-121832 discloses a configuration of an endoscope cleaning/disinfecting apparatus including two limit switches provided at an insertion portion, in which after a chemical bottle is inserted into the insertion portion, a first limit switch detects a position of the chemical bottle immediately before a blade portion cuts into a stopper portion, and a second limit switch detects a completely-inserted position of the chemical bottle at which the blade portion opens the stopper portion of the chemical bottle.

SUMMARY OF THE INVENTION

Briefly, an endoscope cleaning/disinfecting apparatus according to an aspect of the present invention include: a chemical bottle including a chemical storage portion that stores a chemical, a stepped portion provided at a side face of the chemical storage portion, a breakable stopper portion provided at a top face of the chemical storage portion, and a spout portion surrounding an outer periphery of the stopper portion at the top face of the chemical storage portion; an insertion portion allowing the chemical bottle to be inserted from the top face side; a chemical receiving portion provided at the insertion portion, the chemical receiving portion having a diameter larger than that of the spout portion; a blade portion arranged in the chemical receiving portion, the blade portion opening the stopper portion of the chemical bottle inserted in the chemical receiving portion; a first limit switch provided at the insertion portion; and a second limit switch provided at the insertion portion, the second limit switch being located on the blade portion side relative to the first limit switch, wherein: when the chemical bottle is inserted to a first position in the insertion portion, the first limit switch is pressed by the chemical bottle that is in contact with the first limit switch and thereby changes from an OFF state to an ON state to detect the first position; when the chemical bottle is inserted to a second position at which an inner face of the chemical receiving portion and the spout portion are aligned to each other, in the state in which the first limit switch is on, the second limit switch is pressed by the chemical bottle that is in contact with the second limit switch and thereby changes from an OFF state to an ON state to detect the second position; when the chemical bottle is inserted to a third position at which the stopper portion is opened as a result of a set amount of the blade portion cutting into the stopper portion, in the state in which the second limit switch is on, the first limit switch is released by the stepped portion from the pressing by the chemical bottle and thereby changes from the ON state to the OFF state to detect the third position.

The above and other objects, features and advantages of the invention will become more clearly understood from the following description referring to the accompanying drawings.

DETAILED DESCRIPTION OF THE PREFERRED EMBODIMENTS

Embodiments of the present invention will be described below with reference to the drawings.

Figure 1:
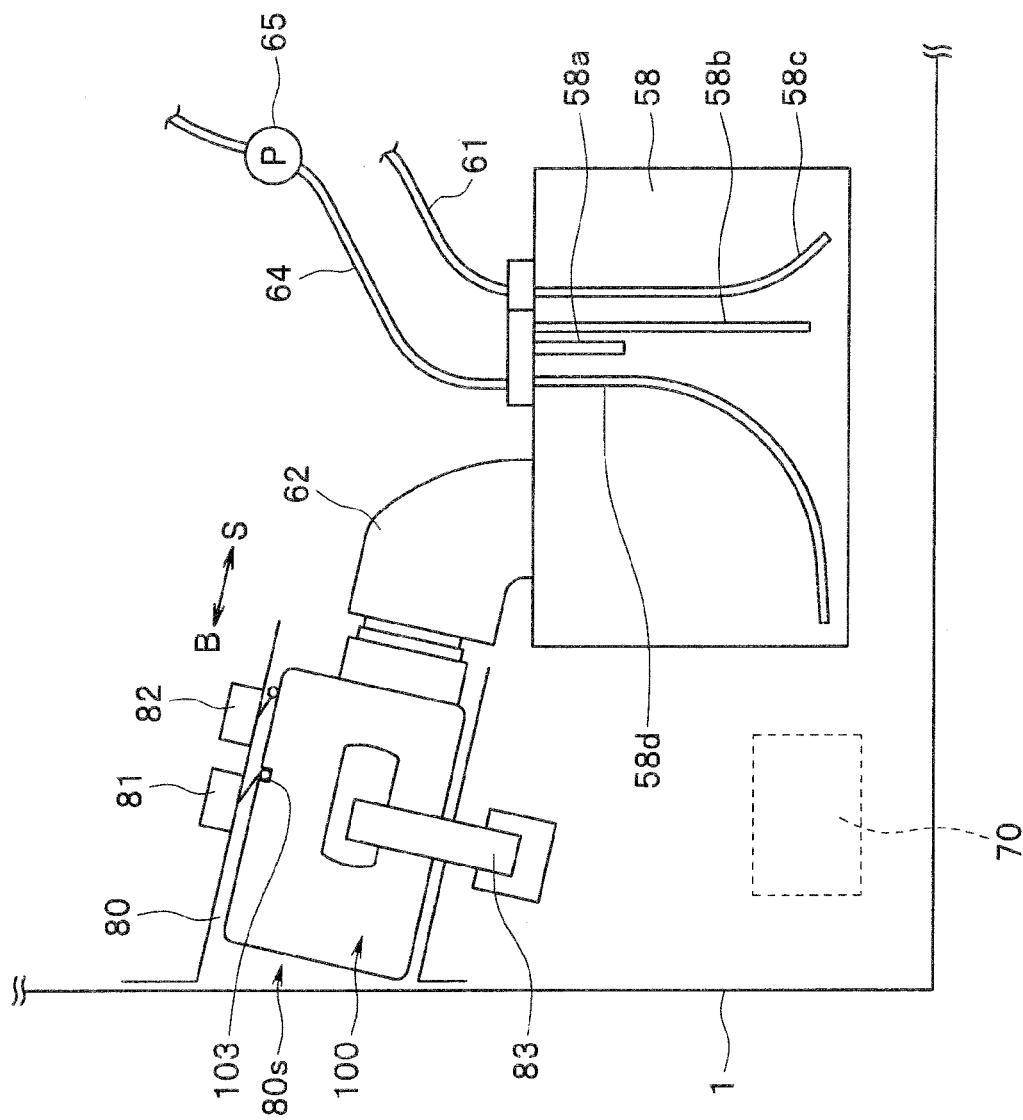
FIG. 1 is a diagram schematically illustrating an overview of a configuration in which a chemical is poured into a chemical tank in an endoscope cleaning/disinfecting apparatus according to an embodiment.
Figure 2:
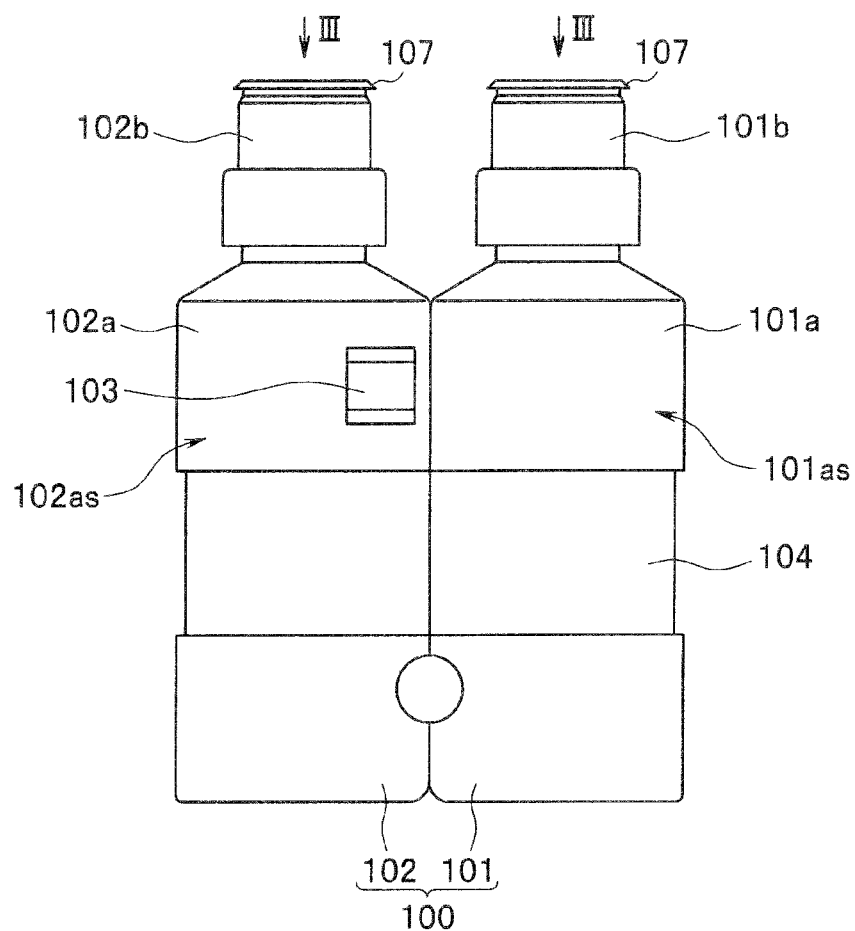
FIG. 2 is an enlarged plan view of a chemical bottle to be inserted into an insertion portion of the endoscope cleaning/disinfecting apparatus in FIG. 1.
Figure 3:
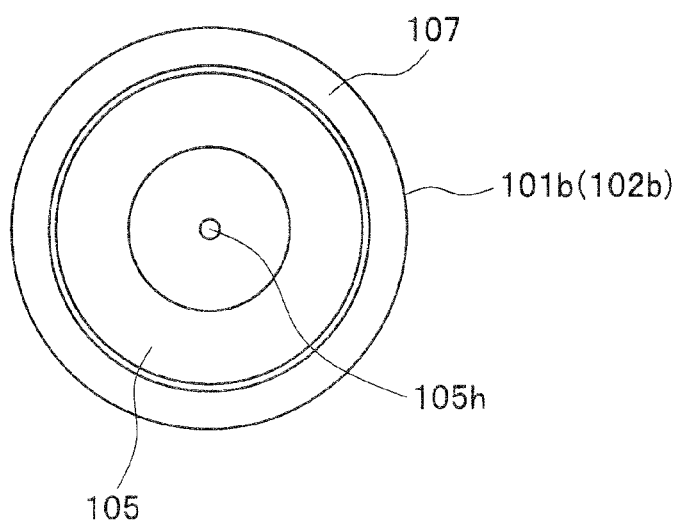
FIG. 3 is an enlarged plan view of a spout portion of the chemical bottle in FIG. 2, viewed in the III direction in FIG. 2.

FIG. 1 is a diagram illustrating an overview of a configuration in which a chemical is poured into a chemical tank in an endoscope cleaning/disinfecting apparatus according to the present embodiment, FIG. 2 is an enlarged plan view of a chemical bottle to be inserted into an insertion portion of the endoscope cleaning/disinfecting apparatus in FIG. 1, and FIG. 3 is an enlarged plan view of a spout portion of the chemical bottle in FIG. 2 viewed in the III direction in FIG. 2.

As illustrated in FIG. 1, an endoscope cleaning/disinfecting apparatus 1 includes a chemical tank 58 in an inner portion thereof Furthermore, an insertion portion 80 allowing a chemical bottle 100 to be inserted from a top face side of the chemical bottle 100 in an insertion direction S is provided at an upper position relative to the chemical tank 58. The insertion portion 80 may have a configuration allowing the chemical bottle 100 to be inserted into the endoscope cleaning/disinfecting apparatus 1 using a non-illustrated cassette tray that can freely be drawn from the endoscope cleaning/disinfecting apparatus 1.

An end of the insertion portion 80 includes an insertion opening 80s formed at an outer surface of a front face of the endoscope cleaning/disinfecting apparatus 1, which is near to a user, and another end of the insertion portion 80 is connected to a chemical receiving portion 62 that makes the insertion portion 80 and the chemical tank 58 be in communication with each other. Although FIG. 1 illustrates a duct line as the chemical receiving portion 62, the shape of the chemical receiving portion 62 is not limited to the duct line, and any shape enabling a chemical introduced from an opened bottle to be guided to the chemical tank 58 may be employed.

The insertion portion 80 is provided at a downward angle from the one end side toward the other end side so that a chemical in the chemical bottle 100 inserted in the insertion portion 80 can be poured by its own weight into the chemical tank 58 via the chemical receiving portion 62.

Furthermore, in an inner portion on the other end side of the insertion portion 80, a later-described blade portion 69 (see FIG. 4) that opens a later-described stopper portion 105 (see FIG. 3) of the chemical bottle 100 inserted to the insertion portion 80 is provided.

Furthermore, at an upper face of the insertion portion 80, a later-described first limit switch 81, and a later-described second limit switch 82 located on the blade portion 69 side relative to the first limit switch 81 are provided.

Figure 6:
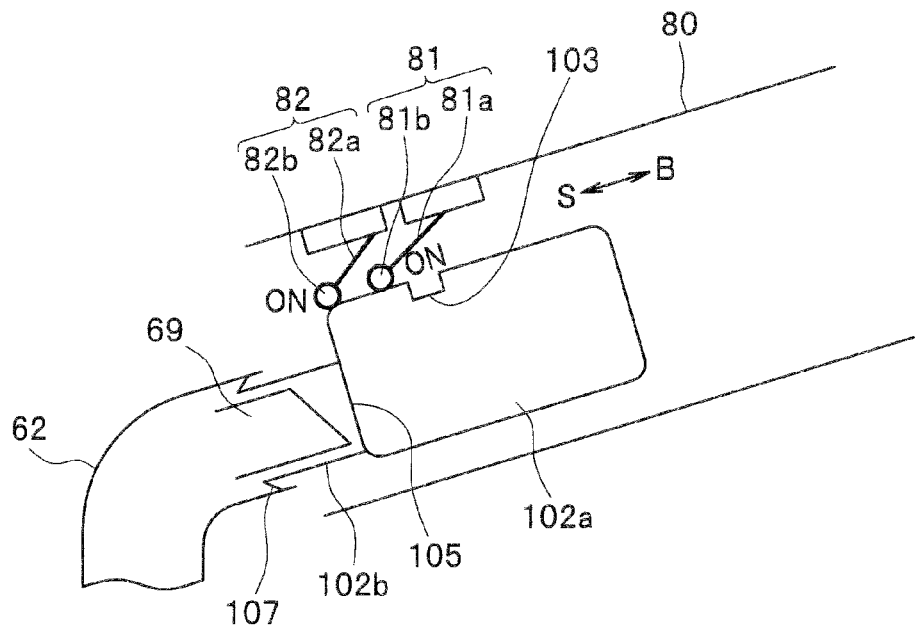
FIG. 6 is a diagram schematically illustrating a state in which the chemical bottle is advanced further in the insertion direction relative to the state in FIG. 5 to reach a second position.

The endoscope cleaning/disinfecting apparatus 1 also includes a locking portion 83 using a known locking arm, which restricts movement of the chemical bottle 100 in a pullout direction B in which the chemical bottle 100 is pulled out of the insertion portion 80 after the chemical bottle 100 is inserted into the insertion portion 80 in an insertion direction S to reach a second position as illustrated in FIG. 6, which will be described later. The chemical bottle 100 can move further in the insertion direction even though the chemical bottle 100 is locked by the locking portion 83.

The configuration of the insertion portion 80 according to the present embodiment may be the same as that of an insertion portion for a chemical bottle conventionally used in an endoscope cleaning/disinfecting apparatus, except for positions at which the first limit switch 81 and the second limit switch 82 are provided. In other words, a size, a shape, and a position of provision, of the blade portion 69, respective shapes of the limit switches 81 and 82, a distance from the insertion opening 80s to a position at which the chemical bottle 100 is locked by the locking portion 83, and a distance from the insertion opening 80s to a position at which the stopper portion 105 of the chemical bottle 100 is opened by the blade portion 69 may be the same as conventional ones.

A plurality of level sensors 58a to 58d that detect an amount of a chemical stored in the chemical tank 58 in a stepwise manner is provided in the chemical tank 58. Information on detection of an amount of a chemical from each of the level sensors 58a to 58d is conveyed to a control section 70 provided in the endoscope cleaning/disinfecting apparatus 1.

Furthermore, an end of a chemical collection duct line 61 used for collecting a chemical in a cleaning/disinfecting bath 4 into the chemical tank 58 is connected to the chemical tank 58, and an end of a chemical duct line 64 used for supplying a chemical from the chemical tank 58 to the cleaning/disinfecting bath 4 is also connected to the chemical tank 58. A chemical pump 65 is interposed at the chemical duct line 64.

As illustrated in FIG. 2, the chemical bottle 100 includes, for example, two chemical bottles 101 and 102. Where a plurality of chemical bottles is used as described above, the chemical bottle 101 and the chemical bottle 102 may integrally be formed so that the chemical bottles 101 and 102 are aligned with each other in terms of their bottom face positions and their top face positions by means of a belt-like member 104. Accordingly, the chemical bottles 101 and 102 are integrally inserted into the insertion portion 80.

It should be understood that the chemical bottle 100 may include one bottle or three or more bottles.

A main portion of the chemical bottle 101 includes a chemical storage portion 101a in which a chemical is stored, a stopper portion 105 (see FIG. 3) that can be broken by the above-described blade portion 69, the stopper portion 105 being provided at a top face of the chemical storage portion 101a, and a tubular spout portion 101b surrounding an outer periphery of the stopper portion 105 at the top face of the chemical storage portion 101a and being provided so as to project from the top face. In the chemical storage portion 101a, for example, a concentrated solution of a disinfectant is stored. Examples of the disinfectant include a peracetic acid.

Furthermore, where a duct line is used as the chemical receiving portion 62, a seal portion 107 that seals a spout portion 101b with respect to the duct line 62 by being brought into water-tight, air-tight contact with an inner peripheral face portion of the duct line 62 by means of an elastic force when the chemical bottle 101 is inserted into the insertion portion 80 may be provided at an outer peripheral edge portion of an projection end of the spout portion 101b.

A main portion of the chemical bottle 102 includes a chemical storage portion 102a in which a chemical is stored, a stopper portion 105 (see FIG. 3) that can be broken by the above-described blade portion 69, the stopper portion 105 being provided at a top face of the chemical storage portion 102a, and a tubular spout portion 102b surrounding an outer periphery of the stopper portion 105 at the top face of the chemical storage portion 102a and being provided so as to project from the top face. In the chemical storage portion 102a, for example, a buffer solution for the disinfectant is stored. The buffer solution has a function that increases the life of the disinfectant in addition to enhancing the ability of disinfectant to penetrate an endoscope.

Furthermore, a seal portion 107 that seals a spout portion 102b with respect to the duct line 62 by being brought into water-tight, air-tight contact with an inner peripheral face portion of the duct line 62 by means of an elastic force when the chemical bottle 102 is inserted into the insertion portion 80 may be provided at an outer peripheral edge portion of an projection end of the spout portion 102b.

Furthermore, a stepped portion 103 is formed on a side face of the chemical storage portion 102a of the chemical bottle 102, more specifically, a side face 102as on the side facing the aforementioned first limit switch 81 and the aforementioned second limit switch 82 when the chemical bottle 102 is inserted into the insertion portion 80.

As illustrated in FIGS. 1 and 2, the stepped portion 103 includes, for example, a recess portion. Furthermore, the stepped portion 103 may be provided on a side face of the chemical storage portion 101a of the chemical bottle 101, more specifically, a side face 101*as* on the side facing the aforementioned first limit switch 81 and the aforementioned second limit switch 82 when the chemical bottle 101 is inserted into the insertion portion 80. In this case, the first limit switch 81 and the second limit switch 82 are brought into contact with the chemical bottle 101.

Furthermore, the chemical bottle 101 and the chemical bottle 102 have a same size and a same shape except for the stepped portion 103 being formed at the chemical bottle 102. It should be understood that the chemical bottle 102 may have a shape and a size that are different from those of the chemical bottle 101.

Furthermore, the shape of the chemical bottle 102 is the same as that of a conventional chemical bottle except for the stepped portion 103 being formed at the chemical bottle 102. Furthermore, where the chemical bottle 100 includes a single chemical bottle, the stepped portion 103 may be provided at a side face of a chemical storage portion of the single chemical bottle, and where the chemical bottle 100 includes three or more chemical bottles, the stepped portion 103 may be provided at a side face of a chemical storage portion of any one of the three or more chemical bottles.

Where a volatile agent such as a peracetic acid is stored, as illustrated in FIG. 3, a pore portion 105*h* is formed in the stopper portion 105 for removal of vapor.

Figure 4:
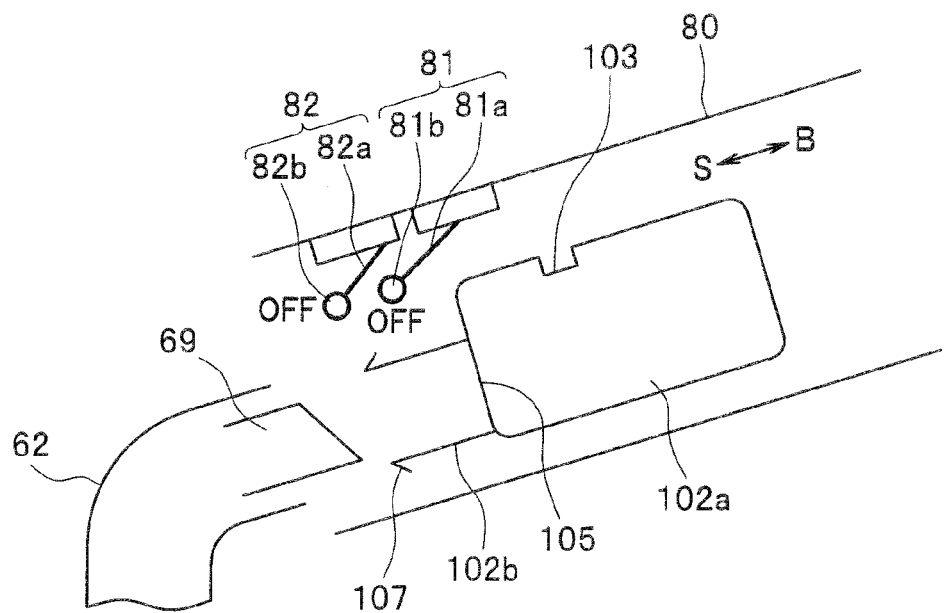
FIG. 4 is a diagram schematically illustrating a state immediately after the chemical bottle is inserted into the insertion portion in FIG. 1.
Figure 5:
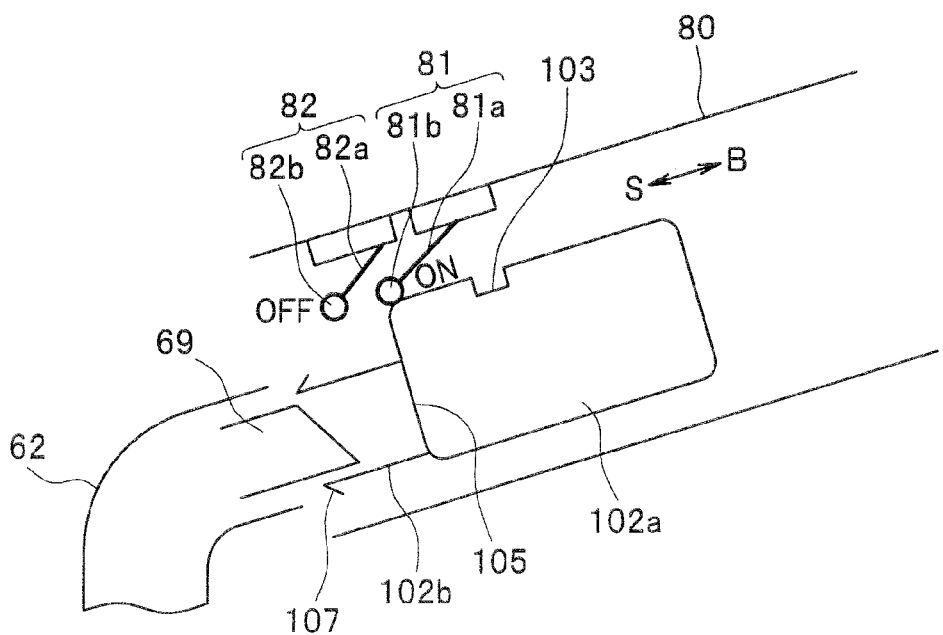
FIG. 5 is a diagram schematically illustrating a state in which the chemical bottle is advanced further in an insertion direction relative to the state in FIG. 4 to reach a first position.
Figure 7:
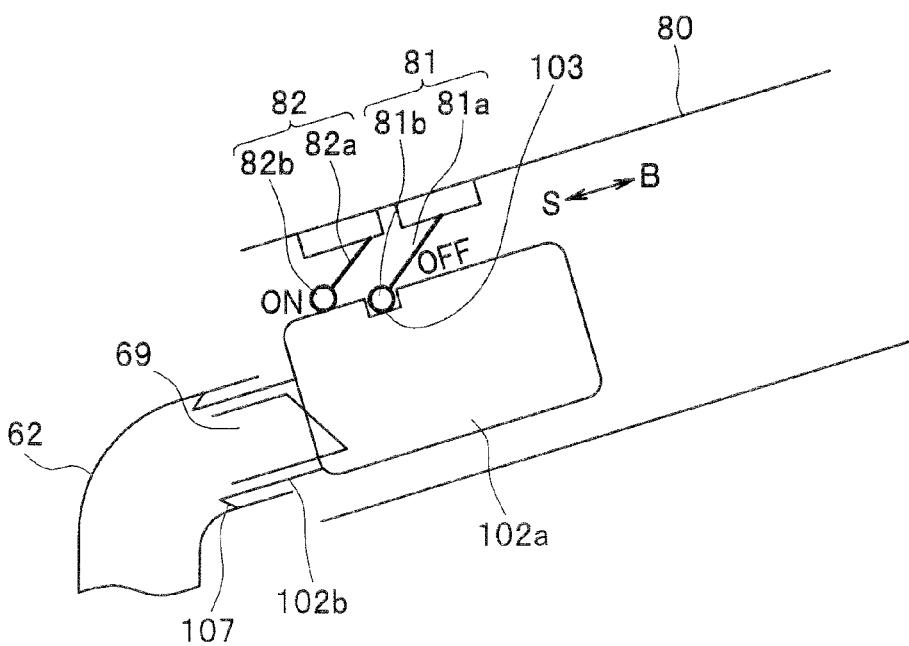
FIG. 7 is a diagram illustrating a state in which the chemical bottle is advanced further in the insertion direction relative to the state in FIG. 6 to reach a third position.

Next, functions of the first limit switch 81 and the second limit switch 82 will be described with reference to FIGS. 4 to 7. FIG. 4 is a diagram schematically illustrating a state immediately after a chemical bottle is inserted to the insertion portion in FIG. 1, FIG. 5 is a diagram schematically illustrating a state in which the chemical bottle is advanced further in the insertion direction relative to the state in FIG. 4 to reach a first position, FIG. 6 is a diagram schematically illustrating a state in which the chemical bottle is advanced further in the insertion direction relative to the state in FIG. 5 to reach a second position, and FIG. 7 is a diagram schematically illustrating a state in which the chemical bottle is advanced further in the insertion direction relative to the state in FIG. 6 to reach a third position.

As illustrated in FIG. 4, the first limit switch 81 and the second limit switch 82 include arm portions 81*a* and 82*a* and contact portions 81*b* and 82*b* provided at extremities of the arm portions 81*a* and 82*a*, respectively.

Furthermore, the first limit switch 81 and the second limit switch 82 are configured so that when the contact portions 81*b* and 82*b* are brought into contact with an outer surface of the chemical storage portion 102*a* of the chemical bottle 102, the first limit switch 81 and the second limit switch 82 are pressed and thereby change their respective switch states from OFF to ON, and each has a function that sends the change of the switch state to the control section 70 (see FIG. 1).

In other words, the first limit switch 81 and the second limit switch 82 include switches that when the contact portions 81*b* and 82*b* are pressed as a result of the contact portions 81*b* and 82*b* being brought into contact with the outer surface of the chemical storage portion 102*a*, make their respective switch states enter an ON state, and when the pressing of the contact portions 81*b* and 82*b* ceases, make their respective switch states enter an OFF state, and each has a function that sends the change of the switch state to the control section 70 (see FIG. 1) to detect a position of the chemical bottle 100.

Furthermore, the contact portion 81*b* of the first limit switch 81 from among the first limit switch 81 and the second limit switch 82 is provided at a position at the upper face of the insertion portion 80 allowing the contact portion 81*b* to fit in the stepped portion 103 including a recess portion formed at the outer surface of the chemical storage portion 102*a* of the chemical bottle 102. The recess portion may be provided at either the chemical bottle 101 or 102. Furthermore, a limit switch may be brought into contact with the chemical bottle 101 only or the chemical bottle 102 only. Furthermore, only the first limit switch 81 may be brought into contact with the chemical bottle 102 while only the second limit switch 82 is brought into contact with the chemical bottle 101.

The switch states of the first limit switch 81 and the second limit switch 82 are both an OFF state when the chemical bottle 100 is not inserted into the insertion portion 80, or as illustrated in FIG. 4, immediately after the chemical bottle 100 is inserted into the insertion portion 80 via the insertion opening 80*s*.

Furthermore, as illustrated in FIG. 5, when the chemical bottle 100 is inserted further in the insertion direction S relative to the state in FIG. 4 to reach a first position at which the contact portion 81*b* of the first limit switch 81 is brought into contact with the outer surface of the chemical storage portion 102*a*, the first limit switch 81 is pressed as a result of the contact portion 81*b* of the first limit switch 81 being brought into contact with the outer surface of the chemical storage portion 102*a*, and thereby changes the switch state from an OFF state to an ON state. In other words, the first limit switch 81 detects the first position of the chemical bottle 100. The result of the detection is sent to the control section 70. Furthermore, at the first position, the switch state of the second limit switch 82 remains in an OFF state.

Furthermore, as illustrated in FIG. 6, in the second limit switch 82, when the chemical bottle 100 is inserted further in the insertion direction S relative to the state in FIG. 5 with the switch state of the first limit switch remaining in the ON state as a result of the pressing and the chemical bottle 100 is thereby moved to a second position at which the contact portion 82*b* of the second limit switch 82 is brought into contact with the outer surface of the chemical storage portion 102*a* and an inner face of the chemical receiving portion 62 and the spout portions 101*b* and 102*b* are aligned to each other, the contact portion 82*b* of the second limit switch 82 is pressed as a result of being brought into contact with the outer surface of the chemical storage portion 102*a*, and the switch state thereby changes from the OFF state to an ON state. In other words, the second limit switch 82 detects the second position of the chemical bottle 100. The result of the detection is sent to the control section 70.

At the second position, the switch states of the first limit switch 81 and the second limit switch 82 are both an ON state. At the second position, the respective seal portions 107 provided at the projection ends of the spout portions 101*b* and 102*b* of the respective chemical bottles 101 and 102 included in the chemical bottle 100 are brought into water-tight, air-tight contact with the inner peripheral face of the chemical receiving portion 62 by means of an elastic force.

Furthermore, at the second position at which the switch state of the second limit switch 82 changes from the OFF state to an ON state, after the change to the ON state, movement of the chemical bottle 100 in the pullout direction B is locked by the above-described locking portion 83. In other words, the second position includes a locking position of the chemical bottle.

As a result, where the chemical bottle 100 is pulled back to the second position illustrated in FIG. 6 before the stopper portion 105 is opened, even if a chemical leaks from the pore portion 105*h* of the stopper portion 105, the leaking chemical is received by the chemical receiving portion 62 because the spout portions 101*b* and 102*b* are aligned to the inner face of the chemical receiving portion 62 by means of the seal portions 107, enabling prevention of the chemical entering the inside of the apparatus. Furthermore, when the chemical bottle 100 is pulled back after the stopper portion 105 is opened, also, the leaking chemical is received by the chemical receiving portion 62, enabling prevention of the chemical entering the inside of the apparatus.

As illustrated in FIG. 7, when the chemical bottle 100 is inserted further in the insertion direction S relative to the state in FIG. 6 to reach a third position, which is a completely-inserted position of the chemical bottle at which the stopper portion 105 is opened by a predetermined amount of the blade portion 69 cutting into the stopper portion 105 with the switch state of the second limit switch 82 remaining in the ON state as a result of the pressing, the contact portion 81b of the first limit switch 81 is fitted in the recess portion included in the stepped portion 103, whereby the contact portion 81b is no longer pressed by the outer surface of the chemical storage portion 102a.

As a result, the switch state of the first limit switch 81 changes from the ON state to the OFF state. In other words, the first limit switch 81 detects the third position of the chemical bottle 100. The result of the detection is sent to the control section 70. At the third position, the switch state of the second limit switch 82 remains in the ON state.

Furthermore, as illustrated in FIG. 5, the control section 70 includes an alarm section that issues a warning when the switch state of the first limit switch 81 changes from an OFF state to an ON state at the first position and then the ON state lasts for a predetermined period of time, for example, ten seconds, that is, the chemical bottle 100 is not moved further in the insertion direction S relative to the state in FIG. 5 and the switch state is not made to enter an OFF state by means of the stepped portion 103 within the predetermined period of time as illustrated in FIG. 7.

Figure 10:
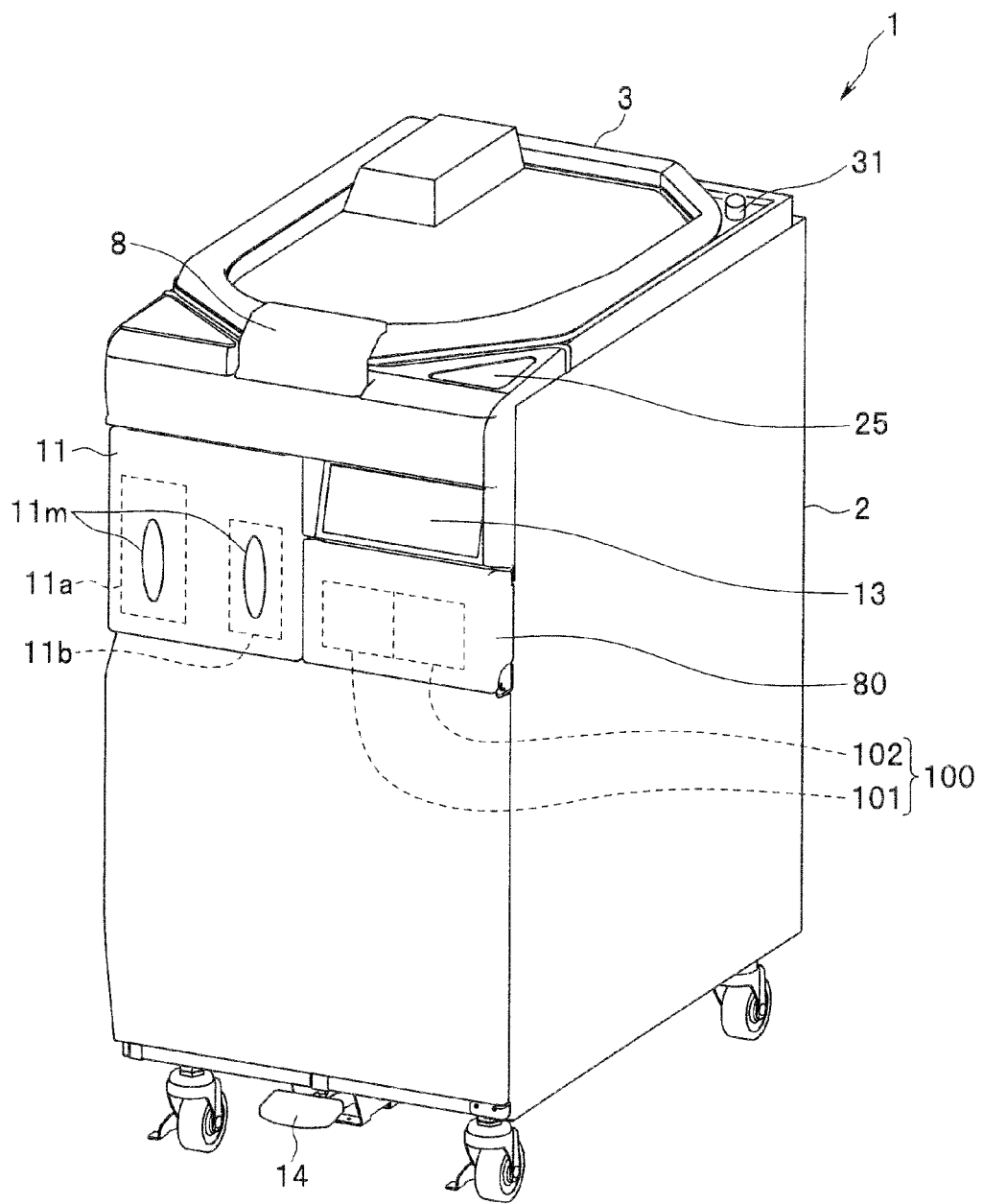
FIG. 10 is a perspective view illustrating an example of appearance of an endoscope cleaning/disinfecting apparatus.

Examples of the warning issued by the control section 70 include ones according to conventional known techniques such as warning display provided on a main operation panel 25 and a sub operation panel 13 as illustrated in FIG. 10, which will be described later, and lighting of a separately provided warning lamp, and a warning tone.

Even if the chemical bottle 100 is left at the first position illustrated in FIG. 5 for a long period of time, the alarm section included in the control section 70 enables a user to be informed of that effect to urge the user to insert the chemical bottle 100 to the third position. Consequently, it is possible to prevent a chemical from the chemical bottle from entering the inside of the endoscope cleaning/disinfecting apparatus 1 as a result of, before the stopper portion 105 is opened, the chemical bottle being moved to a position short of the second position illustrated in FIG. 6 in the pullout direction B and left for a long period of time.

As a variation, a configuration in which the stepped portion 103 includes a recess portion that is larger in the insertion direction S (pullout direction B) than that of the present embodiment, the contact portion 81b of the first limit switch 81 is fitted in the recess portion at the second position and the switch state of the first limit switch 81, which is an ON state at the first position, is thereby changes to an OFF state to detect the second position, and the second limit switch 82 is brought into contact with the chemical bottle 100 with the first limit switch 81 remaining in the OFF state at the third position and the switch state of the second limit switch 82 thereby changes from an OFF state to an ON state to detect the third position may be employed.

As described above, in the present embodiment, the contact portion 81b of the first limit switch 81 is brought into contact with the outer surface of the chemical storage portion 102a of the chemical bottle 102 and the switch state of the first limit switch 81 thereby changes from an OFF state to an ON state to detect the first position of the chemical bottle 100, and the contact portion 82b of the second limit switch 82 is brought into contact with the outer surface of the chemical storage portion 102a of the chemical bottle 102 and the switch state of second limit switch 82 thereby changes from an OFF state to an ON state to detect the second position at which the inner face of the chemical receiving portion and the spout portions are aligned to each other, and the contact portion 81b of the first limit switch 81 is fitted in the recess portion included in the stepped portion 103 formed at the side face of the chemical storage portion 102a of the chemical bottle 102, and the switch state of the first limit switch 81 thereby changes from the ON state to the OFF state to detect the third position of the chemical bottle 100.

According to the above, an endoscope cleaning/disinfecting apparatus 1 is able to be provided including a configuration in which using only two limit switches 81 and 82, a position of the chemical bottle 100 that is short of a second position can be detected by the first limit switch 81 in addition to detection of the second position, which is a locking position of the chemical bottle 100, and a third position, which is a completely-inserted position of the chemical bottle 100, enabling detection of an initial insertion position of the chemical bottle 100.

Furthermore, the present embodiment has been described in terms of a case where the control section 70 issues a warning when after the first limit switch 81 enters an ON state at the first position and the first limit switch 81 does not enter an OFF state at the third position after the elapse of a set period of time.

According to the above, it is possible to reliably inform a user of a state in which the chemical bottle 100 is left at the first position for a long period of time, which may result in chemicals leaking from the pore portions 105h of the stopper portions 105 into the insertion portion 80, and the user can be aware of the state, and thus, it is possible to prevent chemical leakage from chemical bottle 100 to the inside of the endoscope cleaning/disinfecting apparatus 1.

Figure 8:
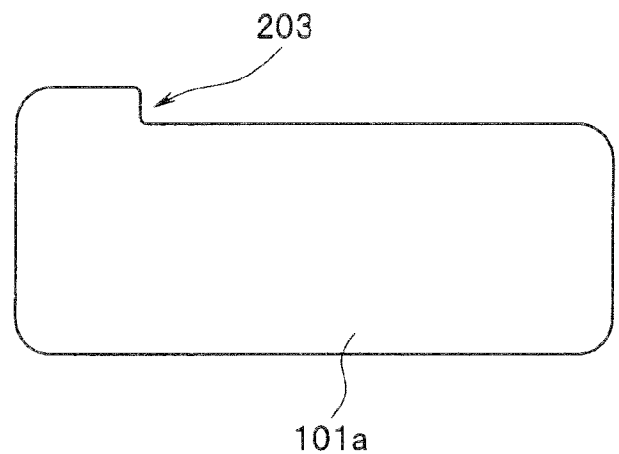
FIG. 8 is a diagram illustrating an overview of a configuration of a variation of a chemical bottle including a stepped portion including a notch.

Another variation will be described below with reference to FIGS. 8 and 9. FIG. 8 is a diagram illustrating an overview of a configuration of a variation of a chemical bottle including a stepped portion including a notch, and FIG. 9 is a diagram illustrating an overview of a configuration of a variation of a chemical bottle including a stepped portion including a projection portion.

The present embodiment has been described above in terms of a case where the stepped portion 103 formed at the chemical bottle 102 includes a recess portion.

Figure 9:
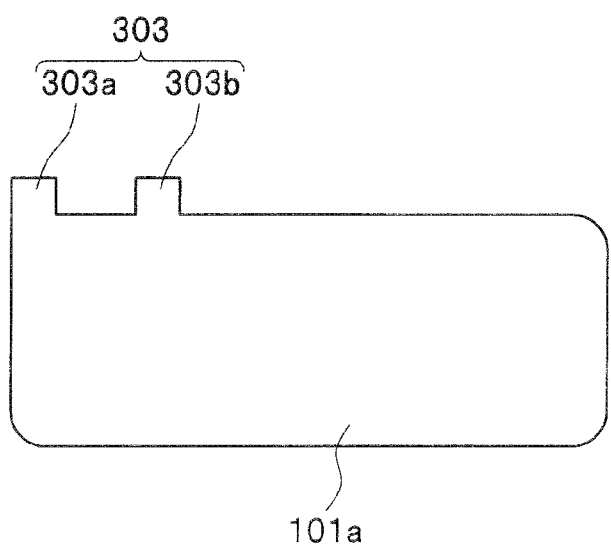
FIG. 9 is a diagram illustrating an overview of a configuration of a variation of a chemical bottle including a stepped portion including a projection portion.

The stepped portion 103 is not limited to these examples, and may have any stepped shape as long as the stepped portion 103 can change the first limit switch 81 to an OFF state at the third position, and the stepped portion 103 may have, for example, a notch 203 such as illustrated in FIG. 8 or a projection portion 303 such as illustrated in FIG. 9.

Where the stepped portion 103 includes the projection portion 303, it is necessary that the first limit switch 81 be configured to climb over a projection portion 303a and thereby change from an OFF state to an ON state, and clime over a projection portion 303b and thereby change from the ON state to the OFF state. In other words, it is necessary that the first limit switch 81 be configured to be switched ON/OFF each time the first limit switch 81 is brought into contact with the projection portion 303a or 303b.

Furthermore, the stepped portion 103 may be one that is formed after the contact portion 81b of the first limit switch 81 is brought into contact with the outer surface of the chemical storage portion 102a.

More specifically, the stepped portion 103 may be configured in such a manner that a part with a small mechanical strength is provided at the side face 102as of the chemical storage portion 102a of the chemical bottle 102, the side face 102as is formed to be a flat face with no step, and after the part with a small mechanical strength is brought into contact with the contact portion 81b of the first limit switch 81 at the third position illustrated in FIG. 7, the part is broken or deformed by the weight of the contact portion 81b, and the stepped portion 103 is thereby formed at the side face 102as.

In this case, the stepped portion 103 formed at the broken or deformed part with a small mechanical strength makes the switch state of the first limit switch 81 enter an OFF state, enabling provision of an effect similar to that of the present embodiment.

Figure 11:
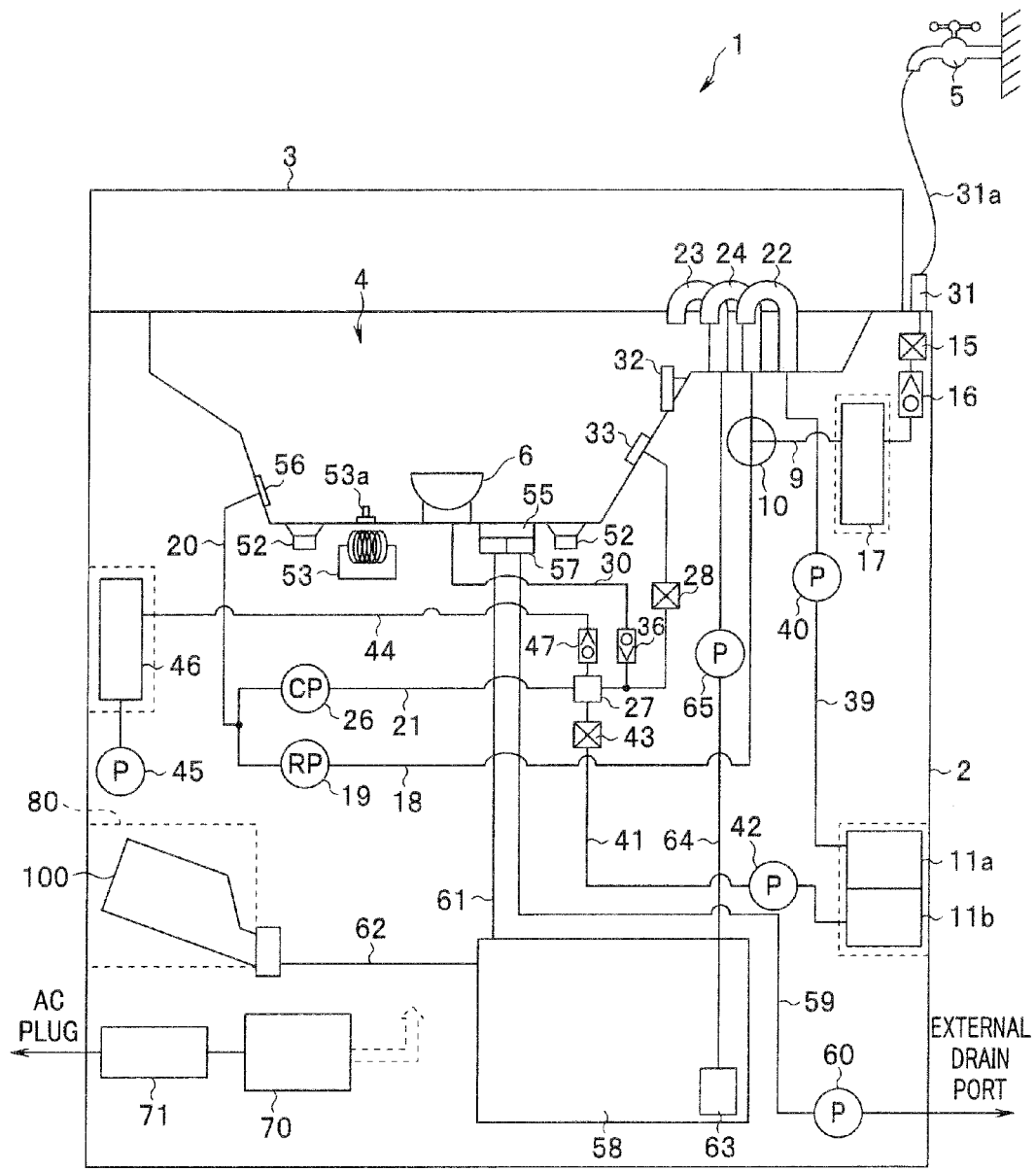
FIG. 11 is a diagram illustrating an example of an internal configuration of an endoscope cleaning/disinfecting apparatus.

An example of a configuration of an endoscope cleaning/disinfecting apparatus including the insertion portion 80 to which the chemical bottle 100 according to the present embodiment is inserted will be described below with reference to FIGS. 10 and 11. FIG. 10 is a perspective view illustrating an example of appearance of the endoscope cleaning/disinfecting apparatus, and FIG. 11 is a diagram illustrating an example of an inner configuration of the endoscope cleaning/disinfecting apparatus.

As illustrated in FIG. 10, a main portion of the endoscope cleaning/disinfecting apparatus 1 includes an apparatus main body 2 and a top cover 3 connected to an upper portion of the apparatus main body 2 via, for example, a non-illustrated hinge in such a manner that the top cover 3 is openable/closable.

Furthermore, in a state in which the top cover 3 is closed on the apparatus main body 2, the apparatus main body 2 and the top cover 3 are secured via, for example, a latch 8 arranged at positions of the apparatus main body 2 and the top cover 3 facing each other.

A detergent/alcohol tray 11 is arranged at an upper portion of a left half portion of a front face of the apparatus main body 2 in FIG. 10, which is near to an operator, in such a manner that the detergent/alcohol tray 11 can be pulled out forward in the apparatus main body 2.

The detergent/alcohol tray 11 accommodates a detergent tank 11a in which a cleaning agent used for cleaning an endoscope is stored and an alcohol tank 11b in which an alcohol used for drying the cleaned/disinfected endoscope is stored. Since the detergent/alcohol tray 11 can be pulled out, liquids can be refilled in the respective tanks 11a and 11b in a predetermined manner.

Two window portions 11m are provided at the detergent/alcohol tray 11, and the window portions 11m enable the operator to check remaining amounts of cleaning agent and alcohol poured into the respective tanks 11a and 11b. The cleaning agent is a concentrated detergent that is diluted to a predetermined concentration with tap water subjected to filtration using a non-illustrated water supply filter.

Furthermore, the above-described insertion portion 80 is provided at an upper portion of a right half of the front face of the apparatus main body 2 in FIG. 10. The insertion portion 80 allows the above-described chemical bottles 101 and 102 to be inserted thereto.

Furthermore, at a portion above the insertion portion 80 at the front face of the apparatus main body 2, the sub operation panel 13 including, e.g., display of cleaning/disinfection time and a button for heating a disinfectant is arranged.

Furthermore, at a lower portion of the apparatus main body 2, a pedal switch 14 for opening the top cover 3, which is closed at the upper portion of the apparatus main body 2, upward via the operator's operation to step on the pedal switch 14.

Furthermore, the main operation panel 25 including a switch for starting an operation to clean/disinfect the apparatus main body 2 and setting switches including a cleaning/disinfection mode selection switch and the like is provided at a portion near an edge of a top face of the apparatus main body 2, which is near to the operator, for example.

Furthermore, a water supply hose connection port 31 to which a non-illustrated water supply hose for supplying tap water to the apparatus main body 2, the water supply hose being connected to a non-illustrated faucet, is connected is provided on the back side of the top face of the apparatus main body 2, which is opposite to the front face near to the operator. A mesh filter for filtrating tap water may be arranged at the water supply connection port 31.

Accordingly, as illustrated in FIG. 11, the endoscope cleaning/disinfecting apparatus 1 is configured so that an end of a water supply hose 31a is connected to the water supply hose connection port 31, and another end of the water supply hose 31a is connected to an external faucet 5 to supply water.

As illustrated in FIG. 11, the water supply hose connection port 31 is in communication with an end of a water supply duct line 9. Another end of the water supply duct line 9 is connected to a three-way solenoid valve 10, and a water-supply solenoid valve 15, a check valve 16 and a water supply filter 17 are interposed at positions part way through the duct line in this order from the water supply hose connection port 31 side.

For the water supply filter 17, a cartridge filtration filter is used for periodical replacement. The water supply filter 17 filters out, e.g., foreign substances and bacteria in tap water passing through the water supply filter 17.

The three-way solenoid valve 10 is connected to an end of a liquid flow duct line 18, communication of the water supply duct line 9 or the liquid flow duct line 18 with a water supply circulation nozzle 24 is switched by means of an inner valve. In other words, the water supply circulation nozzle 24 is in communication with any one of the water supply duct line 9 and the liquid flow duct line 18 via a switching operation of the three-way solenoid valve 10. Furthermore, a liquid flow pump 19 capable of delivering a liquid only, which is a non-self-suction pump having good liquid delivery capability, is interposed at on the other end side of the liquid flow duct line 18.

A circulation port 56 arranged at the cleaning/disinfecting bath 4 is connected to an end of the circulation duct line 20. Another end of the circulation duct line 20 is bifurcated so that the circulation duct line 20 is in communication with the other end of the liquid flow duct line 18 and an end of a channel duct line 21. Another end of the channel duct line 21 is in communication with a port 33 for air-delivery/water-delivery or a forceps opening. Furthermore, although not illustrated, the other end of the channel duct line 21 is connected also to a non-illustrated port for elevating forceps.

A channel pump 26, a channel block 27 and a channel solenoid valve 28 are interposed at positions part way through the channel duct line 21 in this order from the one end side. A cleaning case 6 is connected to an end of a duct line 30 for the case. Another end of the duct line 30 for the case is connected to the channel duct line 21 between the channel block 27 and the channel solenoid valve 28. A relief valve 36 is interposed at the duct line 30 for the case. The channel pump 26 includes a self-suction pump that can deliver either a liquid or a gas at a pressure higher than that of a non-self-suction pump.

A detergent nozzle 22 is connected to an end of a cleaning agent duct line 39, and another end of the cleaning agent duct line 39 is connected to the detergent tank 11a. At a position part way through the cleaning agent duct line 39, a detergent pump 40 including a high-pressure self-suction pump for pumping a cleaning agent up from the detergent tank 11a to the cleaning/disinfecting bath 4 is interposed.

The alcohol tank 11b is connected to an end of an alcohol duct line 41, and the alcohol duct line 41 is connected to a channel block 27 so that the alcohol duct line 41 is in communication with the channel duct line 21 in a predetermined manner.

At the alcohol duct line 41, an alcohol supply pump 42 including a high-pressure self-suction pump for pumping an alcohol up from the alcohol tank 11b to the cleaning/disinfecting bath 4, and a solenoid valve 43 are interposed.

Furthermore, an end of an air duct line 44 for supplying an air from an air pump 45 including a self-suction pump capable of delivering a gas is connected to the channel block 27 so that the air duct line 44 is in communication with the channel duct line 21 in a predetermined manner. Another end of the air duct line 44 is connected to the air pump 45, and at positions part way through the air duct line 44, a check valve 47 and an air filter 46 that is periodically replaced are interposed.

An openable/closable switching valve 57 for discharging, e.g., a cleaning solution to the outside or collecting a disinfectant to the chemical tank 58 via a switching operation of the valve is arranged at a first drain port 55 of the cleaning/disinfecting bath 4.

An end of a drain duct line 59 is connected to a non-illustrated drain hose connected to and thereby is in communication with an external drain port. The switching valve 57 is connected to another end of a drain duct line 59, and a drain pump 60 including a non-self-suction pump is interposed at the drain duct line 59. Furthermore, the switching valve 57 is connected to an end of a chemical collection duct line 61, and another end of the chemical collection duct line 61 is connected to the chemical tank 58.

As described above, the chemical tank 58 is connected also to an end of the chemical receiving portion 62 so that a chemical, for example, a disinfectant, is supplied from the chemical bottle 100. Another end of the chemical receiving portion 62 is connected to a cassette tray 12 in a predetermined manner.

Furthermore, an end of a chemical duct line 64 is provided with a suction filter 63. The chemical tank 58 accommodates the part of the end of the chemical duct line 64 in a predetermined manner Another end of the chemical duct line 64 is connected to a disinfectant nozzle 23, and a chemical pump 65 including a high-pressure self-suction pump for pumping a disinfectant up from the chemical tank 58 to the cleaning/disinfecting bath 4 is interposed at a position part way through the chemical duct line 64.

Below a bottom face 50t of the cleaning/disinfecting bath 4, as described above, for example, two ultrasound transducers 52 and a heater 53 are provided. Furthermore, for adjustment of a temperature of the heater 53, a temperature detection sensor 53a is provided at a substantial center of the bottom face 50t of the cleaning/disinfecting bath 4.

The heater 53 is intended to heat the disinfectant stored in the cleaning/disinfecting bath 4 and circulating within the apparatus, to a predetermined temperature. For a disinfectant, there is a proper temperature at which a disinfection effect of the disinfectant can most highly be expected. The disinfectant heated by the heater 53 to the predetermined temperature, which is the proper temperature, can effectively disinfect the respective duct lines in the endoscope and the apparatus main body 2.

Furthermore, the temperature detection sensor 53a detects the temperature of the disinfectant stored in the cleaning/disinfecting bath 4 and circulating within the apparatus, and conveys the result of the detection to the control section 70. Then, based on the result of the detection from the temperature detection sensor 53a, the control section 70 performs control to drive or stop the heater 53 so as to maintain the disinfectant at the predetermined temperature.

Furthermore, a power supply 71 supplied with power from an external AC plug, and the control section 70 electrically connected with the power supply 71 are provided in an inner portion of the endoscope cleaning/disinfecting apparatus 1. The control section 70 is supplied with various signals from the main operation panel 25 and the sub operation panel 13, and controls driving of, e.g., the above-described respective pumps and the above-described respective solenoid valves.

In particular, the control section 70 includes a water supply duct line disinfecting program for performing known water removal, disinfection and rinsing of at least the inside of the water supply duct line 9 via the circulation duct line 20 and the channel duct line 21, as well as collecting at least tap water or the disinfectant in the cleaning/disinfecting bath 4 to the chemical tank 58 via the chemical collection duct line 61 or discharging water from the external drain port via the drain duct line 59, and also performs known control of driving of the respective valves and the respective pumps according to the water supply duct line disinfecting program.

The control section 70 also includes an all-duct line disinfecting program for disinfecting the insides of all the duct lines in the endoscope cleaning/disinfecting apparatus 1, and an endoscope cleaning/disinfecting program for cleaning/disinfecting an endoscope duct line of an endoscope connected to the port 33 via a tube.

The present invention is not limited only to the above-described embodiments, and various variations of the present invention can be carried out without departing from the scope and spirit of the present invention.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope cleaning/disinfecting apparatus comprising:
    a chemical bottle including a chemical storage portion that stores a chemical, a stepped portion provided at a side face of the chemical storage portion, a breakable stopper portion provided at a top face of the chemical storage portion, and a spout portion surrounding an outer periphery of the stopper portion at the top face of the chemical storage portion;
    an insertion portion allowing the chemical bottle to be inserted from the top face side;
    a chemical receiving portion provided at the insertion portion;
    a blade portion arranged in the chemical receiving portion, the blade portion opening the stopper portion of the chemical bottle inserted in the chemical receiving portion;
    a first limit switch provided at the insertion portion, the first limit switch detecting a first position as an insertion initial position in an insertion direction of the chemical bottle which is brought into contact with an outer surface of the chemical storage portion after the chemical bottle is started to be inserted into the insertion portion, and a third position as an insertion completion position located farther than the first position in the insertion direction of the chemical bottle, at which the stopper portion is opened by the blade portion cutting into the stopper portion by a set amount; and a second limit switch provided at the insertion portion, the second limit switch being located on the blade portion side with respect to the first limit switch, the second limit switch detecting a second position in the insertion direction of the chemical bottle, at which an inner face of the chemical receiving portion and the spout portion are aligned to each other, wherein:

when the chemical bottle is inserted to the first position in the insertion portion, the first limit switch is pressed by the chemical bottle that is in contact with the first limit switch and thereby changes from an OFF state to an ON state to detect that the chemical bottle is inserted to the first position in the insertion portion, and sends information of a change of a switch state to a control section;

when the chemical bottle is inserted from the first position to the second position in the state in which the first limit switch is ON, the second limit switch is pressed by the chemical bottle that is in contact with the second limit switch and thereby changes from an OFF state to an ON state to detect that the chemical bottle is inserted to the second position, and sends information of a change of a switch state to the control section; and when the chemical bottle is inserted from the second position to the third position in the state in which the second limit switch is ON, the first limit switch is released by the stepped portion from the pressing by the chemical bottle and thereby changes from the ON state to the OFF state to detect that the chemical bottle is inserted to the third position in the insertion portion, and sends information of a change of a switch state to the control section, and the control section determines a position of the chemical bottle in the insertion portion based on the switch state of the first limit switch and the switch state of the second limit switch, and wherein the control section is configured to determine that the chemical bottle is in one of the first position, the second position and the third position based on the information of a change of a switch state, and to perform control based on the determination that the chemical bottle is in one of the first position, the second position and the third position.

2. The endoscope cleaning/disinfecting apparatus according to claim 1, wherein when the ON state of the first limit switch lasts for a predetermined period of time after the change of the first limit switch from the OFF state to the ON state at the first position, the control section determines that the chemical bottle is left at the first position for the predetermined period of time without being inserted to the third position or the second position and issues a warning.

3. The endoscope cleaning/disinfecting apparatus according to claim 1, further comprising a locking portion that restricts movement of the chemical bottle in a pullout direction in which the chemical bottle is pulled out of the insertion portion, wherein the locking portion locks the movement of the chemical bottle in the pullout direction after the change of the second limit switch from the OFF state to the ON state at the second position.

4. The endoscope cleaning/disinfecting apparatus according to claim 1, wherein the stepped portion includes a recess portion provided at the side face of the chemical storage portion.

5. An endoscope cleaning/disinfecting apparatus in which a chemical bottle is insertable, the chemical bottle including a chemical storage portion that stores a chemical, a stepped portion provided at a side face of the chemical storage portion, a breakable stopper portion provided at a top face of the chemical storage portion, and a spout portion surrounding an outer periphery of the stopper portion at the top face of the chemical storage portion, the endoscope cleaning/disinfecting apparatus comprising:

an insertion portion allowing the chemical bottle to be inserted from the top face side;

a chemical receiving portion provided at the insertion portion;

a blade portion arranged in the chemical receiving portion, the blade portion opening the stopper portion of the chemical bottle inserted in the chemical receiving portion;

a first limit switch provided at the insertion portion, the first limit switch detecting a first position as an insertion initial position in an insertion direction of the chemical bottle which is brought into contact with an outer surface of the chemical storage portion after the chemical bottle is started to be inserted into the insertion portion, and a third position as an insertion completion position located farther than the first position in the insertion direction of the chemical bottle, at which the stopper portion is opened by the blade portion cutting into the stopper portion by a set amount; and a second limit switch provided at the insertion portion, the second limit switch being located on the blade portion side with respect to the first limit switch, the second limit switch detecting a second position in the insertion direction of the chemical bottle, at which an inner face of the chemical receiving portion and the spout portion are aligned to each other and an outer periphery of the spout portion is brought into water-tight and air-tight contact with the inner face of the chemical receiving portion, wherein:

when the chemical bottle is inserted to the first position in the insertion portion, the first limit switch is pressed by the chemical bottle that is in contact with the first limit switch and thereby changes from an OFF state to an ON state to detect that the chemical bottle is inserted to the first position in the insertion portion, and sends information of a change of a switch state to a control section;

when the chemical bottle is inserted from the first position to the second position in the state in which the first limit switch is ON, the second limit switch is pressed by the chemical bottle that is in contact with the second limit switch and thereby changes from an OFF state to an ON state to detect that the chemical bottle is inserted to the second position, and sends information of a change of a switch state to the control section; and when the chemical bottle is inserted from the second position to the third position in the state in which the second limit switch is ON, the first limit switch is released by the stepped portion from the pressing by the chemical bottle and thereby changes from the ON state to the OFF state to detect that the chemical bottle is inserted to the third position in the insertion portion, and sends information of a change of a switch state to the control section, and the control section determines a position of the chemical bottle in the insertion portion based on the switch state of the first limit switch and the switch state of the second limit switch, and wherein the control section is configured to determine that the chemical bottle is in one of the first position, the second position and the third position based on the information of a change of a switch state, and to perform control based on the determination that the chemical bottle is in one of the first position, the second position and the third position.

* * * * *